United States Patent
Nakaji et al.

(10) Patent No.: US 10,912,504 B2
(45) Date of Patent: Feb. 9, 2021

(54) NEAR-INFRARED SPECTROSCOPY AND DIFFUSE CORRELATION SPECTROSCOPY DEVICE AND METHODS

(71) Applicants: Canon U.S.A. Inc., Melville, NY (US);
The General Hospital Corporation, Boston, MA (US); Haruo Nakaji, Boston, MA (US); Maria Angela Franceschini, Winchester, MA (US); David Boas, Winchester, MA (US); Erin Buckley, Atlanta, GA (US); Pei-Yi Lin, Cambridge, MA (US); Stefan Carp, Revere, MA (US)

(72) Inventors: Haruo Nakaji, Boston, MA (US); Maria Angela Franceschini, Winchester, MA (US); David Boas, Winchester, MA (US); Erin Buckley, Atlanta, GA (US); Pei-Yi Lin, Cambridge, MA (US); Stefan Carp, Revere, MA (US)

(73) Assignees: CANON U.S.A., INC., Melville, NY (US); THE GENERAL HOSPITAL CORPORATION, Boston, MA (US)

( * ) Notice: Subject to any disclaimer, the term of this patent is extended or adjusted under 35 U.S.C. 154(b) by 369 days.

(21) Appl. No.: 15/111,721

(22) PCT Filed: Jan. 14, 2015

(86) PCT No.: PCT/US2015/011444
§ 371 (c)(1),
(2) Date: Jul. 14, 2016

(87) PCT Pub. No.: WO2015/109005
PCT Pub. Date: Jul. 23, 2015

(65) Prior Publication Data
US 2016/0345880 A1    Dec. 1, 2016

Related U.S. Application Data

(60) Provisional application No. 61/927,371, filed on Jan. 14, 2014.

(51) Int. Cl.
*A61B 5/1455* (2006.01)
*A61B 5/026* (2006.01)
(Continued)

(52) U.S. Cl.
CPC ........ *A61B 5/14552* (2013.01); *A61B 5/0261* (2013.01); *A61B 5/14546* (2013.01);
(Continued)

(58) Field of Classification Search
CPC ... A61B 5/1455; A61B 5/0205; A61B 5/0261; A61B 5/14546; A61B 5/14553;
(Continued)

(56) References Cited

U.S. PATENT DOCUMENTS 6,076,010 A    6/2000  Boas et al.
6,246,892 B1   6/2001  Chance
(Continued)

FOREIGN PATENT DOCUMENTS

EP    0615723 A1    4/1993
JP    08-038460 A   2/1996
(Continued)

OTHER PUBLICATIONS

Boas, D., "Handbook of Biomedical Optics", Chapter 10, pp. 195-216, CRC Press, 2011.
(Continued)

*Primary Examiner* — Chu Chuan Liu
(74) *Attorney, Agent, or Firm* — Canon U.S.A., Inc., IP Division

(57) ABSTRACT

There is provided herewith an apparatus, probe, and method for the combination of near-infrared spectroscopy (NIRS)
(Continued)

and diffuse correlation spectroscopy (DCS). The apparatus, probe and method allow for the simultaneous detection of NIRS and DCS.

21 Claims, 5 Drawing Sheets

(51) Int. Cl.
 *A61B 5/00* (2006.01)
 *A61B 5/145* (2006.01)
(52) U.S. Cl.
 CPC ........ *A61B 5/14553* (2013.01); *A61B 5/4064* (2013.01); *A61B 5/4866* (2013.01); *A61B 5/7225* (2013.01); *A61B 5/7278* (2013.01); *A61B 2562/0238* (2013.01)
(58) Field of Classification Search
 CPC . A61B 5/14532; A61B 5/4866; A61B 5/7225; A61B 5/7278; A61B 5/4064
 See application file for complete search history.

(56) References Cited

U.S. PATENT DOCUMENTS

| | | | |
|---|---|---|---|
| 7,120,481 | B2 | 10/2006 | Keller et al. |
| 7,184,614 | B2 | 2/2007 | Slatkine |
| 8,022,378 | B2 | 9/2011 | Cadwalader et al. |
| 8,082,015 | B2 | 12/2011 | Yodh et al. |
| 8,175,668 | B1 | 5/2012 | Nabutovsky et al. |
| 8,320,981 | B1 | 11/2012 | Mayer et al. |
| 8,938,279 | B1* | 1/2015 | Heaton, II ......... A61B 5/14552 600/323 |
| 9,380,967 | B2 | 7/2016 | Esenaliev et al. |
| 2004/0122300 | A1 | 6/2004 | Boas et al. |
| 2006/0063995 | A1* | 3/2006 | Yodh ................. A61B 5/14551 600/323 |
| 2006/0222224 | A1 | 10/2006 | Ohashi |
| 2008/0312533 | A1 | 12/2008 | Balberg et al. |
| 2009/0292210 | A1 | 11/2009 | Culver et al. |
| 2010/0241006 | A1 | 10/2010 | Choi et al. |
| 2011/0245687 | A1 | 10/2011 | Rensen |
| 2012/0184831 | A1 | 7/2012 | Seetamraju et al. |
| 2012/0277559 | A1 | 11/2012 | Kohl-Bareis et al. |
| 2013/0016575 | A1 | 1/2013 | Campbell et al. |

FOREIGN PATENT DOCUMENTS

| | | |
|---|---|---|
| JP | 2004-504092 A | 2/2004 |
| JP | 2006-218013 A | 8/2006 |
| JP | 2010-240298 A | 10/2010 |
| WO | 2013090658 A1 | 6/2013 |

OTHER PUBLICATIONS

Buckley, E., et al, "A Novel Combined Frequency-Domain Near-Infrared Spectroscopy and Diffuse Correlation Spectroscopy System," in Biomedical Optics 2014, Optical Society of America 2014.
Carp, SA et al., "Validation of Optical Measurements of Cerebral Blood Flow and Volume with SPION and ASL fMRI: Implications for CMRO2 Changes During Hypercapnia" Proc. Intl. Soc. Mag. Reson. Med., 2009, vol. 17.
Diop, M et al. "Calibration of Diffuse Correlation Spectroscopy with a Time-Resolved Near-Infrared Technique to Yield Absolute Cerebral Blood Flow Measurements", Biomedical Optical Express, Jul. 1, 2011, vol. 2, No. 7.
Diop, M., et al. "Time-Resolved Near-Infrared and Diffuse Correlation Spectroscopy for Continuous Measurement of Absolute Cerebral Blood Flow", pp. 772, abstract found at http://kenes.com/brain2011/abstracts/pdf/772.pdf.
Durduran, T., et al., "Diffuse optics for tissue monitoring and tomography", Reports on Progress in Physics, Jul. 2010, vol. 73, No. 7.
Lynch, J., et al., "Noninvasive optical quantification of cerebral venous oxygen saturation in humans", Acad Radiol. Feb. 2014, pp. 162-167, vol. 21, No. 2.
Franceschini, M., et al., "Assessment of infant brain development with frequency-domain near-infrared spectroscopy", Pediatric Research, May 2007, pp. 546-551, vol. 61, No. 5, pt. 1.
Gagnon, L. et al., "Quantification of the cortical contribution to the NIRS signal over the motor cortex using concurrent NIRS-fMRI measurements", Neuriomage, Feb. 15, 2012, pp. 3933-3940, vol. 59, No. 4.
Grant, P.E., et al., "Increased cerebral blood volume and oxygen consumption in neonatal brain injury", Journal of Cerebral Blood Flow and Metabolism, 2009, vol. 29, pp. 1704-1713.
Yu, G., "Diffuse Correlation Spectroscopy (DCS): A Diagnostic Tool for Assessing Tissue Blood Flow in Vascular-Related Diseases and Therapies", Current Medical Imaging Review, 2012, pp. 194-210, vol. 8, No. 3.
Yu, G., et al., "Non-Invasive Measurements of Deep Tissue Hemodynamics in Human Skeletal Muscle", Optical Society of America, 2004, document from U. Penn http://www.lrsm.upenn.edu/pmi/nonflash-ver/project/muscleNF.html.
Yu, G. "Near-Infrared Diffuse Correlation Spectroscopy in Cancer Diagnosis and Therapy Monitoring", Journal of Biomedical Optics, Jan. 2012, vol. 17, No. 1.
Gurley, K., et al., "Noninvasive Optical Quantification of Absolute Blood Flow, Blood Oxygenation, and Oxygen Consumption Rate in Exercising Skeletal Muscle", J. Biomed. Opt., Jul. 2012, vol. 17, No. 7.
Lin, P., et al., "Non-invasive Optical Measurement of Cerebral Metabolism and Hemodynamics in Infants", J. Vis. Exp., Mar. 14, 2013, vol. 73.
Munk, N et al., "Noninvasively measuring the hemodynamic effects of massage on skeletal muscle: A novel hybrid nearinfrared diffuse optical instrument", J. Bodywork & Movement Ther., 2012, pp. 22-28, vol. 16.
Zirak, P., et al., "Effects of acetazolamide on the micro- and macro-vascular cerebral hemodynamics: a diffuse optical and transcranial Doppler ultrasound study", Biomedical Optics Express, Dec. 1, 2010, pp. 1443-1459, vol. 1, No. 5.
Roche-Labarbe, N., et al., "Noninvasive optical measures of CBV, StO(2), CBF index, and rCMRO(2) in human premature neonates' brains in the first six weeks of life", Hum Brain Mapp., Mar. 2010, vol. 31, No. 3.
Roche-Labarbe, N., et al., "Near-infrared spectroscopy assessment of cerebral oxygen metabolism in the developing premature brain", Journal of Cerebral Blood Flow and Metabolism, 2012, pp. 481-488, vol. 32.
Shang, Yu., et al., "Noninvasive Optical Characterization of Muscle Blood Flow, Oxygenation, and Metabolism in Women with Fibromyalgia", Arthritis Research & Therapy, 2012, vol. 14.
Strangman, G., Depth Sensitivity and Source-Detector Separations for Near Infrared Spectroscopy Based on the Colin27 Brain Template, PLOS ONE, NIRS Depth and Spatial Sensitivity, Aug. 2013, vol. 8, issue 8.
Li, T., et al., "Simultaneous measurement of deep tissue blood flow and oxygenation using noncontact diffuse correlation spectroscopy flow-oximeter", Scientific Report, 2013, vol. 3, Article No. 1358.
Verdecchia, K et al., "Quantifying the Cerebral Metabolic Rate of Oxygen by Combining Diffuse Correlation Spectroscopy and Time-Resolved Near-Infrared Spectroscopy" J. Biomed. Opt., Feb. 2013, vol. 18, No. 2.
Walter, B., et al., "Simultaneous Measurement of Local Cortical Blood Flow and Tissue Oxygen Saturation by Near infra-red Laser Doppler Flowmetry and Remission Spectroscopy in the Pig Brain", Acta Neurochir Suppl., 2002, vol. 81.
Optical Topography System ETG-4000; http://www.hitachimedical.com/products/OpticalTopography/?WT.ac=med_mg_pro_ot visited Jul. 5, 2016.

(56) References Cited

OTHER PUBLICATIONS

Prahl, S., "Optical Absorption of Hemoglobin", Dec. 15, 1999 at http://omlc.ogi.-edu/spectra-/hemoglobin-/index.html), visited Jul. 5, 2016.
Selb, J., et al., "Sensitivity of near-infrared spectroscopy and diffuse correlation spectroscopy to brain hemodynamics: simulations and experimental findings during hypercapnia", Neurophotonics, Jul.-Sep. 2014, vol. 1, No. 1.

* cited by examiner

NEAR-INFRARED SPECTROSCOPY AND DIFFUSE CORRELATION SPECTROSCOPY DEVICE AND METHODS

CROSS-REFERENCE TO RELATED APPLICATION(S)

This application is a national stage application of PCT/US15/011444 filed 14 Jan. 2015 and claims priority to U.S. Provisional Application Serial Number 61/927371 filed Jan. 14, 2014, the content of each of which are herein incorporated by reference in its their entirety.

STATEMENT REGARDING FEDERALLY SPONSORED RESEARCH

This application may have been made with government support under EB001954 and HD042908 awarded by the National Institute of Health. The government may have certain rights in the invention.

FIELD OF THE INVENTION

This application relates generally to medical devices and methods and in particular to a device combining near-infrared spectroscopy (NIRS) and diffuse correlation spectroscopy (DCS) and its use.

BACKGROUND

Near infrared spectroscopy (NIRS) can be used for the measurement of the oxygen saturation in the tissue. For example, NIRS can be used for the assessment of brain function by detecting the change in oxygen saturation (SO2). Since SO2 is a surrogate for cerebral oxygen consumption, this measurement can provide information related to brain function through a quick and non-invasive route. However, the oxygen saturation measured by NIRS may not highly correlate with brain functions compared with the cerebral oxygen consumption. Additionally, SO2 measurements are not always particularly sensitive when the measurements occur hours after brain injury occurs since oxygen consumption and delivery reach equilibrium after acute events.

Thus, it is better to use the oxygen consumption for the assessment of brain function instead of simply using the $SO_2$ measurement. Neuron energy consumption is derived largely from tissue oxidative metabolism, and neural hyperactivity and cell death cause a change in oxygen consumption, which can be measured as cerebral oxygen metabolism ($CMRO_2$). Thus, measures of $CMRO_2$ are reflective of neuronal viability and provide critical diagnostic information, making $CMRO_2$ an ideal target for measurement of brain health. Oxygen consumption is calculated from the oxygen saturation measured by NIRS in combination with parameters including blood flow, which can be measured by using the diffuse correlation spectroscopy (DCS) system.

The measurement procedure of the combined NIRS and DCS system includes measuring locations in frontal, temporal and partiental areas of the patient's brain. A process for this measurement is described by Lin, P. Y., et al., (*J. Vis. Exp.* (73), e4379, 2013), which is incorporated by reference in its entirety herein. First, the patient's hair was parted to expose a section of the patient scalp. Then, the probe was attached to the patient's head and the light sources and the detectors of the NIRS system were turned on. To obtain a $SO_2$ measurement, the NIRS measurement was acquired for 16 seconds. After turning off the light sources and the detector of the NIRS system, the light source and the detectors of the DCS system were turned on. For the probe system described by Lin P. Y. et al., the source and detector fibers for DCS were on the same probe as the NIRS source and detector fibers. However, the DCS source and detector fibers were aligned separately and in a different location than the NIRS source and detector fibers. Therefore, the probe had to be slightly shifted before the DCS measurement in order to acquire the data at the same location on the patient's head. The data of the DCS measurement was acquired for 10 seconds. As described by Lin, P. Y. et al., this process, including taking both the NIRS and DCS measurements, was repeated three times at each of the chosen frontal, temporal and partiental locations on the head.

This design does not allow simultaneous measurement of NIRS and DCS for several reasons, including that the probe must be shifted in order to measure at the same location and the fact that the NIRS and DCS detectors cannot discriminate between the different signals, requiring that both the source and the detector of the two technique are alternatively turned off when the measurements are obtained. Thus, the NIRS and DCS measurements cannot be operated simultaneously.

A combined NIRS and DCS system was also reported by Peyman Zirak et al., (*Biomedical Optics Express, Vol.* 1, No. 5, pp. 1443-1456, 2010). This system described 0.5 seconds NIRS measurement followed by a 3 sec. DCS measurement, where measurements from two probes placed on either side of a forehead were carried out simultaneously. In each probe, the line between the NIRS source and detector fibers in the probe was crossed with the line between the DCS source and detector fibers so that the measurements were carried out at roughly the same tissue volume. However, the area including all fibers was quite large. Thus, the probe as described by Peyman Zirak et al. cannot be applied to a patient's scalp where hair is present since the part of a person's scalp is too narrow for the probe to fit. The size of this probe is particularly problematic when attempting to take NIRS and DCS measurements of infants. Additionally, simultaneous NIRS and DCS measurements are not possible.

Thus, a sophisticated method to quantify cerebral oxygen metabolism is needed. Such a system would provide quantifiable results with improved detection of, for example, brain health, brain development, and response to therapy and particularly to for improved detection in neonates. Preferably, this system would be more usable by a physician or technician. There is also needed an apparatus and method for reducing acquisition time and the need for either several instruments or the need to turn different sources and detectors on and off while performing the method. There is further a need for an apparatus that can take NIRS and DCS measurements simultaneously.

SUMMARY

According to at least one embodiment of the invention, there is provided an integrated device comprising a first optical waveguide configured to deliver light at a first wavelength towards a tissue, and wherein the first optical waveguide is configured to deliver light at a second wavelength towards the tissue or wherein the device contains a second optical waveguide configured to deliver light at the second wavelength towards the tissue. The first and second wavelengths and any additional wavelengths configured for absorption spectroscopy are referred to as SO2 light. The device also comprises a third optical waveguide configured to deliver a light at a third wavelength towards the tissue, the light at a third wavelength referred to as CBF light. The third wavelength is either longer or shorter than both the first wavelength and second wavelength. A fourth optical waveguide is configured to transmit one or more SO2 lights scattered from the tissue and a fifth optical waveguide is configured to transmit the CBF light scattered from the tissue. The device also comprises a probe tip coupled to the distal end of each of the first, second (if present), third, fourth, and fifth optical waveguides (all the waveguides), wherein the distal ends of all the waveguides are aligned linearly at the probe tip. This integrated device is capable of detecting the SO2 and CBF lights simultaneously.

According to at least one embodiment, there is provided an integrated device comprising: one or more light sources (first light source), having at least a first wavelength within the range of 660 to 910 nm and a second wavelength within the range of 660 to 910 nm (SO2 light); one or more waveguides configured to direct the SO2 light towards a tissue; one or more detectors (first detector) configured to detect SO2 light which is transmitted from the tissue; a second light source having a third wavelength that is greater than each of the wavelengths of SO2 light (CBF light); a waveguide configured to direct the CBF light towards a tissue; a second detector configured to detect light scattered from the tissue at the fourth wavelength; a processor adapted to quantify temporal intensity fluctuations in detected CBF light. This integrated device is capable of detecting NIR light and CBF light simultaneously.

There is also provided a method of simultaneously measuring cerebral tissue oxygenation ($StO_2$) and cerebral blood flow index ($CBF_i$) in a tissue of a subject. The determination of $StO_2$ in the tissue of the subject comprising the steps:
  transmitting at least two lights (SO2 lights), having at least two different wavelengths within the range of 660 to 910 nm, into the tissue,
  detecting light after it has traveled through the tissue, and
  determining the difference between the intensity of the transmitted light and the detected light at each of the at least two different wavelengths, and
  determining the difference in attenuation to obtain $StO_2$;
The determination of $CBF_i$ in the tissue of the subject comprising the steps:
  transmitting a third light into the tissue, wherein the third light has a third wavelength that is greater than each of the wavelengths of the SO2 lights,
  sensing a quantity of the light intensity scattered from the tissue at the third wavelength,
  determining the CBFi.
This method is particularly advantageous since $StO_2$ and $CBF_i$ are determined simultaneously.

There is also provided a device for simultaneous detection comprising: a first optical waveguide configured to deliver light at a first wavelength towards a tissue; a second optical waveguide configured to deliver light at a second wavelength towards a tissue; a third optical waveguide configured to deliver light at a third wavelength towards a tissue, a fourth optical waveguide configured to transmit light scattered from the tissue at the first and second wavelengths; a fifth optical waveguide configured to transmit light scattered from the tissue at the first and second wavelengths; a sixth optical waveguide configured to transmit light scattered from the tissue at the third wavelength; a probe tip coupled to the distal end of each of the first, second, third, fourth, fifth, and sixth optical waveguides (all the waveguides), wherein the distal ends of all the waveguides are aligned linearly at the probe tip; a first detector, in optical communication with the fourth optical waveguide, configured to detect light at the first and second wavelengths; a second detector, in optical communication with the fifth optical waveguide, configured to detect light at the first and second wavelengths; a third detector, in optical communication with the sixth optical waveguide, configured to detect light scattered from the tissue at the third wavelength; and a processor adapted to quantify temporal intensity fluctuations in detected light by the second detector.

Further features of the present invention will become apparent from the following description of exemplary embodiments with reference to the attached drawings.

BRIEF DESCRIPTION OF DRAWINGS

Further objects, features and advantages of the present invention will become apparent from the following detailed description when taken in conjunction with the accompanying figures showing illustrative embodiments of the present invention.

DETAILED DESCRIPTION OF THE INVENTION

The present invention provides an apparatus and method for the combination of near-infrared spectroscopy (NIRS) and diffuse correlation spectroscopy (DCS).

Near-Infrared Spectroscopy and Tissue Oxygen Saturation

Near-infrared spectroscopy (NIRS) is a spectroscopic method that uses the near-infrared region of the electromagnetic spectrum. Medical application of NIRS is the non-invasive measurement of the amount and oxygen content of hemoglobin. NIRS is widely used for the assessment of brain function.

Hemoglobin is the oxygen-transport metalloprotein in the blood cells. Hemoglobin picks up oxygen in the lungs then carries the oxygen from the lungs to the tissues and releases it. Oxyhemoglobin is hemoglobin having an additional oxygen molecule. Deoxyhemoglobin is hemoglobin that is not combined with oxygen.

Figure 1:
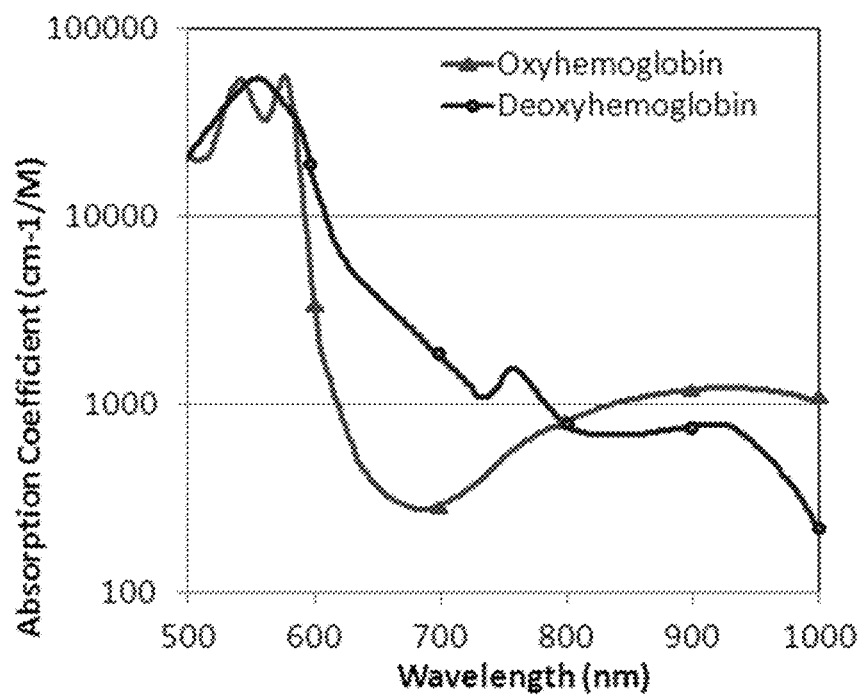
FIG. 1 provides the absorption spectra of oxyhemoglobin and deoxyhemoglobin.

Red blood cells will contain different concentrations of oxyhemoglobin and deoxyhemoglobin. The absorption spectrum of the blood reflects this difference in concentration. The NIRS system measures the oxygen saturation by utilizing the absorption spectra of oxyhemoglobin and deoxyhemoglobin. Since the absorption spectrum of oxyhemoglobin in the near-infrared wavelength region is different from that of deoxyhemoglobin (see FIG. 1 which shows the absorption spectra of oxyhemoglobin and deoxyhemoglobin, see http://omlc.ogi.edu/spectra/hemoglobin/index.html), a wavelength range from about 660 nm to about 910 nm is particularly useful in distinguishing the different concentrations of oxyhemoglobin and deoxyhemoglobin and then determining oxygen content in blood. A wavelength range of 660 nm to about 830 nm is also particularly contemplated. While it is possible to use wavelengths outside the wavelength range from about 660 nm to about 910, nm such as between 250 nm and 1.5 µm. Additionally, as the wavelength moves further into the IR region and past 830 nm, 850 nm, or 910 nm, detectors such as PMT detectors have reduced efficiency at collecting the scattered light. Therefore, unless a detector with greater IR efficiency is used, the use of longer wavelengths is not preferred.

In order to measure the absorption spectrum of blood using NIRS, it is preferable to use multiple wavelength light source(s). For example, eight laser diodes having eight different wavelengths were used by Lin P. Y., et al. In another experiment, Grant, P. E. et al., (J. Cerebral Blood Flow & Metab. (2009) 29, 1704-1713) used eight wavelengths and eight laser diodes having different wavelengths from each other to measure the absorption spectrum of blood.

Multiple source-detector distances can be used to quantify absorption and scattering coefficients with this system. These source-detector separations may be chosen to optimize the depth of penetration of the NIR radiation. For example, source-detector separations of 1 cm, 1.5 cm, 2 cm, and 2.5 cm are chosen to quantify absorption and scattering coefficients, which includes the cerebral cortex in neonates. In other examples, source-detector separations of, for example, two or more of 1.5 cm, 2 cm, 2.5 cm, 3.0 cm, 3.5 cm, and 4.0 cm are chosen. In some embodiments, a source-detector separation of 3.0 cm or less is preferred. In other embodiments, fewer or more source-detector separations are used to perform NIRS.

The absorption coefficients ($\mu_a(\lambda)$) of the blood at each chosen wavelength are calculated from the power of the SO2 light coming from the tissue 306 and the power of the SO2 light incident on the tissue 306. The concentrations of oxyhemoglobin and deoxyhemoglobin as well as the total hemoglobin are then calculated by using the following equations:

$$\mu_a(\lambda_1) = \varepsilon_{oxy}(\lambda_1) \cdot [\text{oxyHb}] + \varepsilon_{deoxy}(\lambda_1) \cdot [\text{deoxyHb}] + \varepsilon_{water}(\lambda_1) \cdot [\text{Water}] \quad (1)$$

$$\mu_a(\lambda_n) = \varepsilon_{oxy}(\lambda_n) \cdot [\text{oxyHb}] + \varepsilon_{deoxy}(\lambda_n) \cdot [\text{deoxyHb}] + \varepsilon_{water}(\lambda_n) \cdot [\text{Water}] \quad (2)$$

$$[\text{totalHb}] = [\text{oxyHb}] + [\text{deoxyHb}] \quad (3)$$

where $\mu_a(\lambda)$ is a blood absorption coefficient as a function of wavelength, $\varepsilon_{oxy}(\lambda)$ and $\Sigma_{deoxy}(\lambda)$ are absorption coefficients of oxyhemoglobin and deoxyhemoglobin as a function of wavelength, $\varepsilon_{water}(\lambda)$ is an absorption coefficient of water as a function of wavelength, [oxyHb] is a concentration of oxyhemoglobin, [deoxyHb] is a concentration of deoxyhemoglobin, [totalHb] is a concentration of total hemoglobin, and [Water] is a concentration of water.

The tissue oxygen saturation is the ratio between the concentrations of oxyhemoglobin and total hemoglobin:

$$StO_2 = \frac{[oxyHb]}{[totalHb]} \quad (4)$$

Thus, the oxygen saturation is determined using NIRS.

Diffuse Correlation Spectroscopy and Cerebral Blood Flow Index

In some cases, oxygen saturation may be insensitive to the assessment of brain function. In order to solve this issue, a diffuse correlation spectroscopy (DCS) system can be combined to the NIRS system. This combination of measurements allows for the calculation of cerebral metabolic rate of oxygen (CMRO$_2$), which is an important marker for brain function and brain health. CMRO$_2$ is more sensitive to measure brain function than StO$_2$ and is a parameter measured by the combined NIRS and DCS system. As mentioned above, the NIRS system measures the oxygen saturation in the tissue. On the other hand, DCS system measures the velocity of blood flow. DCS measures speckle fluctuations of near-infrared diffuse light in the tissue where the speckle fluctuation depends on the motions of red blood cells. Therefore, DCS can non-invasively measure the velocity of blood flow in the deep tissue and thus provide the cerebral blood flow index (CBFi). While DCS measures the effective Brownian diffusive coefficient. Although the unit of the effective Brownian diffusive coefficient is different from the unit of blood flow, the change in that correlates with the change in blood flow [Boas, 2011]. Thus, for measurements of blood in capillary instead of in the artery or vein, the cross-section is unlikely to change since, in general, capillaries do not have smooth muscle. DCS measurements are described, for example, in U.S. Pat. No. 6,076,010, which is incorporated herein by reference in its entirety.

It is contemplated that blood flow measured from sources other than the cerebral cortex, such as from the pial veins found above the cortex is accounted for in the calculation of CMRO2. For example, a correction factor may be used to remove pial contamination of the signal to obtain a more accurate cerebral blood flow measurement. See Gagnon et al., Neuriomage 2012; 59(4) 3933-3940, herein incorporated by reference in its entirety. Alternatively, the relative content of cerebral and pial or other blood flow may be attributed to measurements at different source-detector separations and the non-cerebral concentrations and this consideration taken into account when calculating CMRO2. See Strangeman, Li, and Zhang, (201) PLOS One, 8(8) e66319, herein incorporated by reference in its entirety.

Oxygen Consumption

The devices and methods provided herein are particularly advantageous in that they allow for the determination of oxygen consumption that can be more accurate calculated than previously determined by using data obtained from measurements of both NIRS and DCS. Oxygen consumption is determined using hemoglobin concentration, blood flow index, arterial oxygenation, and tissue oxygenation. As discussed above, tissue oxygenation is determined by NIRS measurements and blood flow index is determined with DCS measurements. Additional systemic parameters can also be used in determining oxygen consumption. Hemoglobin concentration, which can be determined by a blood test and arterial oxygenation which can be determined using a pulse oxymeter are also measured Thus, $CMRO_2$ may be calculated by using the following equation:

$$CMRO_2 = CMRO_2 = \frac{HGB \times CBF_i \times (SaO_2 - StO_2)}{4 \times MW_{Hb} \times \beta} \quad (5)$$

where HGB is the hemoglobin concentration measured by a blood test, $SaO_2$ is the arterial oxygen saturation (oxygenation) measured by a pulse oxymeter, $StO_2$ is the tissue oxygen saturation measured by NIRS, $MW_{Hb}$=64,500 [g/mol] is the molecular weight of hemoglobin, $\beta$ ($\approx$0.84) is the percent contribution of the venous compartment to the hemoglobin oxygenation measurement. CBFi is the cerebral blood flow index measured by DCS. Therefore, by combining the NIRS measurement of $StO_2$ and the DCS measurement of $CBF_i$, $CMRO_2$ can be estimated. See Lin P. Y. et al., J Vis Exp (73): e4379.

The calculated $CMRO_2$ may also be relative CMRO2 (rCMRO2), and may be calculated by using the following equation:

$$rCMRO_2 = \frac{CMRO_2}{CMRO_{2o}} = \frac{HGB}{HGB_o} \cdot \frac{CBF_i}{CBF_{io}} \cdot \frac{SaO_2 - StO_2}{SaO_{2o} - StO_{2o}} \quad (6)$$

where each of the parameters are defined above and where the subscript "o" defines the reference value. See Nadege Roche-Labarbe et al., Journal of Cerebral Blood Flow & Metabolism (2012) 32, 481-488.

Probe Design

Figure 3A:
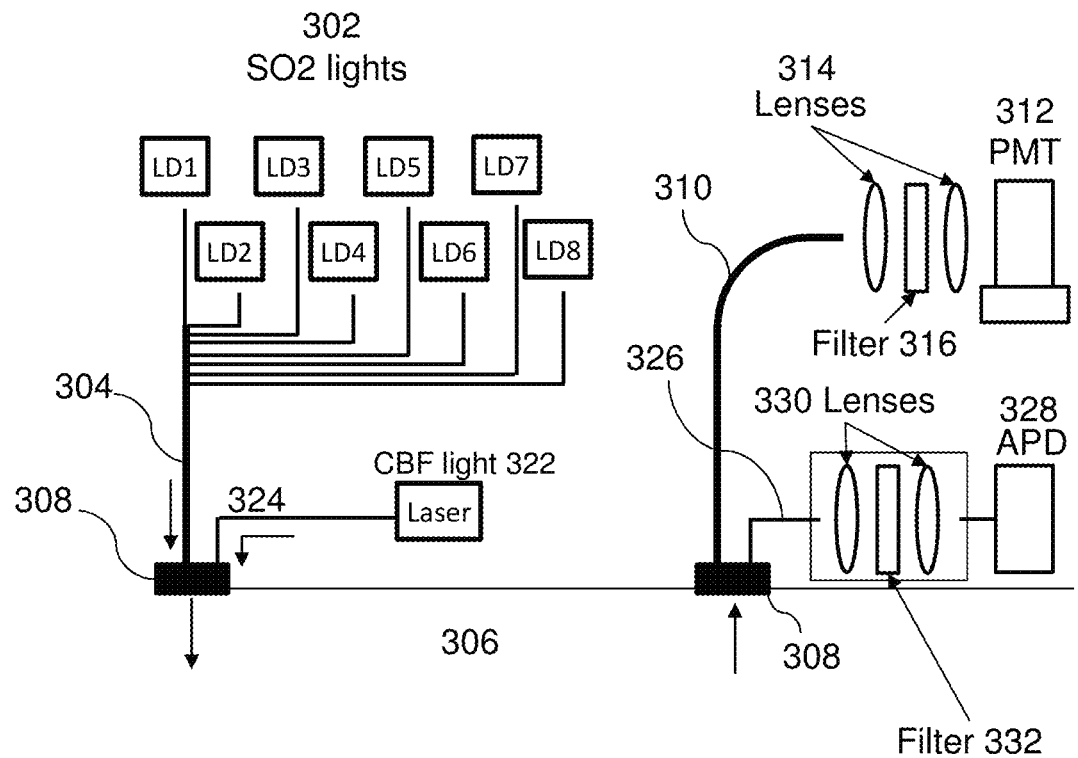
FIG. 3A is a schematic diagram of an exemplary NIRS and DCS system.

FIG. 3A shows an exemplary embodiment of the combined NIRS and DCS system (300). In this example, eight laser diodes (302) having eight different wavelengths are used for the NIRS measurement. The light output from the multiple wavelength light source(s) (302) is delivered via an optical fiber (304) where it connects to the tissue (306) through the probe tip (308). The light radiated to the tissue (306) is scattered in the tissue. A part of the scattered light is collected by the optical fiber (310) at the probe tip (308) and input to the photomultiplier tube used as the NIRS detector (312) after passing through an optional lense system that includes collimating lenses (314) and a low pass filter (316).

The light source for the DCS measurement (322) as exemplified in FIG. 3A is different from that for the NIRS measurement. The coherent length of the DCS laser source (322) is long, because the DCS measurement utilizes the interference of multiply scattering light. The light emitted from the DCS light source (CBF light source (322) is delivered by the optical fiber (324). The CBF light is radiated to the tissue (306) and scattered into the tissue. A part of the scattered CBF light is collected by the optical fiber (326) and input to the avalanche photodiode detector (APD) for the DCS measurement (328). Optionally, the light path includes a lense system that contains collimating lenses (330) and a high pass filter (332).

The scattered SO2 light inputs into both the optical fibers (310) and (326). The scattered CBF light inputs into both the optical fibers (310) and (326). However, the filter in front of the PMT (316) passes through only SO2 signal, attenuate the intensity of CBF light. As a result, only SO2 light is input to the PMT in the embodiment shown in FIG. 3A. If the filter (332) is put in front of the APD, that filter (332) passes through only CBF light and attenuate the intensity of SO2 light. As a result, only CBF light is input to the APD. Therefore, it is not necessary to turn off the light source of DCS while the NIRS light source is turned on.

It is better that the NIRS and DCS measurements are operated at the almost same time and the almost same location, because the $CMRO_2$ is calculated from the oxygen saturation measured by NIRS and the blood flow measured by DCS. In order to do that, the probe configuration is important.

Figure 3B:
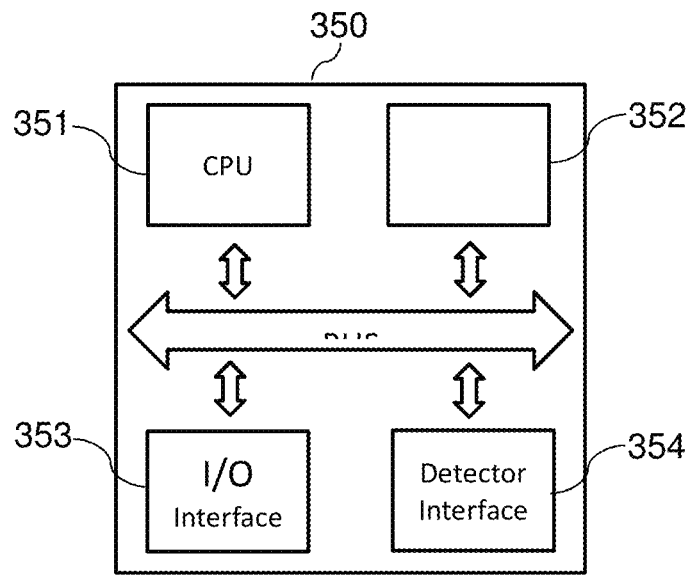
FIG. 3B is a more detailed schematic diagram of an exemplary computer system for the NIRS and DCS system.

As shown in FIG. 3B, the computer system 350 includes CPU 351, Storage/RAM 352, I/O Interface 353 and Detector Interface 354. Also, Computer system 350 may comprise one or more devices. For example, the one computer may include components 351, 352 and 353 and other computer may include component 354.

The CPU 351 is configured to read and perform computer-executable instructions stored in the Storage/RAM 352. The computer-executable instructions may include those for the performance of the methods and/or calculations described herein. For example, CPU 351 calculates speckle fluctuations of near-infrared diffuse light as temporal intensity fluctuations based on the detected light by the detector for the CBF light. Or, CPU 351 calculates CMRO2, as oxygen consumption, using data obtained from analyzing the SO2 lights and the CBF light.

Storage/RAM 352 includes one or more computer readable and/or writable media, and may include, for example, a magnetic disc (e.g., a hard disk), an optical disc (e.g., a DVD, a Blu-ray), a magneto-optical disk, semiconductor memory (e.g., a non-volatile memory card, flash memory, a solid state drive, SRAM, DRAM), an EPROM, an EEPROM, etc. Storage/RAM 352 may store computer-readable data and/or computer-executable instructions. The components of the computer system 350 communicate via a bus.

The I/O interface 353 provides communication interfaces to input and output devices, which may include a keyboard, a display, a mouse, a printing device, a touch screen, a light pen, an optical storage device, a scanner, a microphone, a camera, a drive, communication cable and a network (either wired or wireless).

The detector interface 354 also provides communication interfaces to input and output devices, which may include photomultiplier tube (PMT) 312, an avalanche photodiode detector (APD) 328. Also, the function of detector may be realized by computer executable instructions (e.g., one or more programs) recorded on a Storage/RAM 352.

Probe Tip Arrangement

Figure 4:
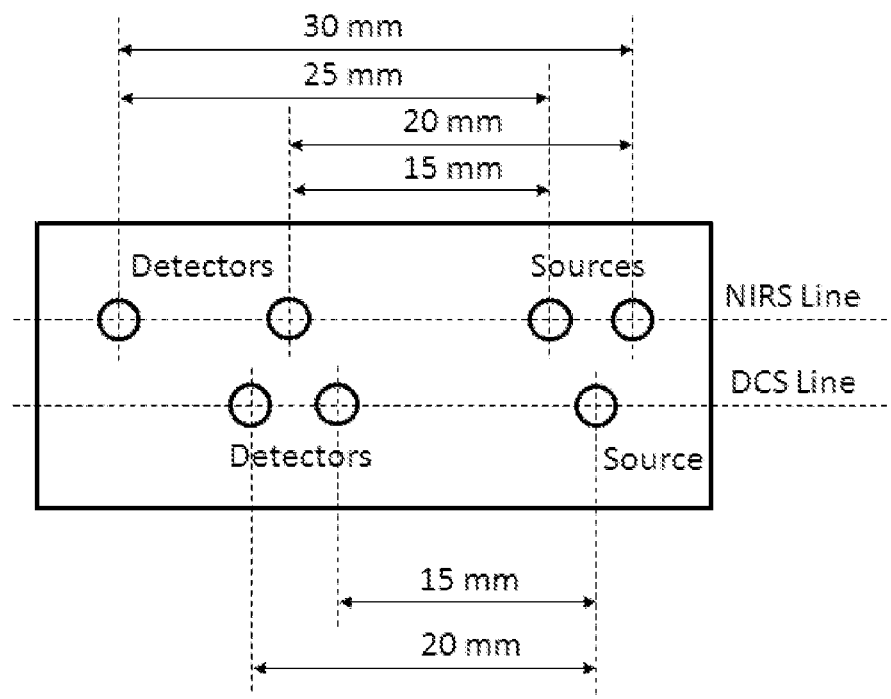
FIG. 4 is a schematic diagram of a probe described in Lin P. Y., et al., which was used in the apparatus combining NIRS and DCS system for newborns. The NIRS and DCS fibers are placed side by side.

FIG. 4 shows the tip of the probe (40) described by in Lin et al. The surface shown in FIG. 4 is placed on the head. The feature of the arrangement of fibers shown in FIG. 4 is that the NIRS source (41) and detector fibers (42) are aligned in the different line from the NIRS source (43) and detector fibers (44). Therefore, in order to acquire the data at the same location, the probe is slightly shifted since the NIRS line (45) and DCS line (46) are physically separated. In this embodiment, the separation is approximately 5 mm. Thus, for any measurements where the NIRS and DCS measurements are taken at the same location and the NIRS and DCS measurements cannot be operated simultaneously.

Figure 5:
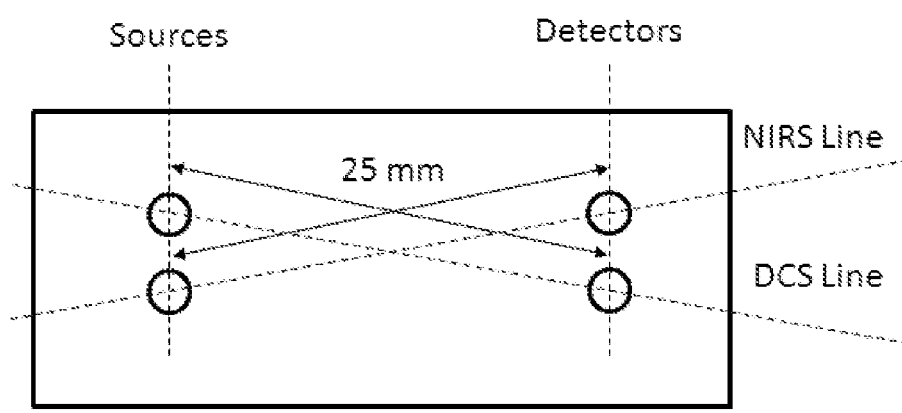
FIG. 5 is a schematic diagram of a probe described in Peyman Zirak et al., that was used in an apparatus combining NIRS and DCS where the NIRS line and DCS lines crisscross.

FIG. 5 shows the probe used by Peyman Zirak et al (50). In order to operate the NIRS and DCS measurements simultaneously, the line (55) between the NIRS source (51) and detector fibers (52) is crossed the line (56) between the DCS source (53) and detector fibers (54). In Peyman Zirak et al, three laser sources were combined in one fiber bundle (51) and two NIRS detectors (52) are used with a single source-detector separation of 2.5 cm (55). Two probes according to FIG. 5 were placed symmetrically on the forehead of adult patients to measure oxyhemoglobin and deoxyhemoglobin concentrations.

Because the area including all fibers is large, it is difficult to apply the probe shown in either previously disclosed FIG. 4 or FIG. 5 to a part with the hair. Hair scatters the light strongly. Thus, if hair is inserted between the optical fiber and the tissue, the power of the light is decreased and the efficacy of the measurement is decreased. In practicing the methods as described herein, the patient's hair is preferably combed to a part where the probe is attached to the scalp. However, the area of the scalp thus exposed by the part is narrow. Therefore, the probe area including all fibers should also be narrow. With a narrow probe, the probe may be placed on the head and both NIRS and DCS measurements may be taken, either simultaneously or sequentially, without the need to adjust the probe position.

Figure 6:
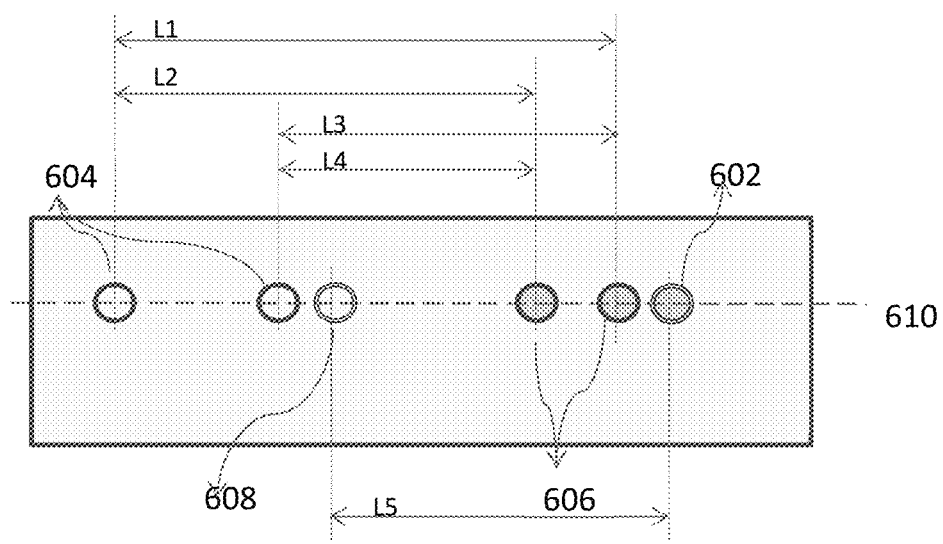
FIG. 6 is an exemplary schematic diagram of a probe of the present invention combining NIRS and DCS where the NIRS and DCS fibers are all within a single line.

Thus, in various embodiments as described herein, the optical fibers for light radiation and detection for both NIRS and DCS are arranged in the single line. As exemplified in FIG. 6, an exemplary probe is shown for the combination of NIRS and DCS that is particularly useful for simultaneous measurements. In this embodiment, the linear arrangement between each of the source and detector probes is shown. Thus, the DCS source (602) is in line with the DCS detector (608), the NIRS sources (606) are in line with the NIRS detector (604) and both the NIRS and DCS sources and detectors are found on a single linear line (610). As shown in FIG. 6, this arrangement provides multiple different spacing between the NIRS source/detector pairs (L1, L2, L3, and L4). In one example, these lengths are L1=30 mm, L2=25 mm, L3=20 mm, and L4=15 mm. The DCS source/detector pair spacing, L5, is also shown and, is 20 mm in one example.

Figure 7:
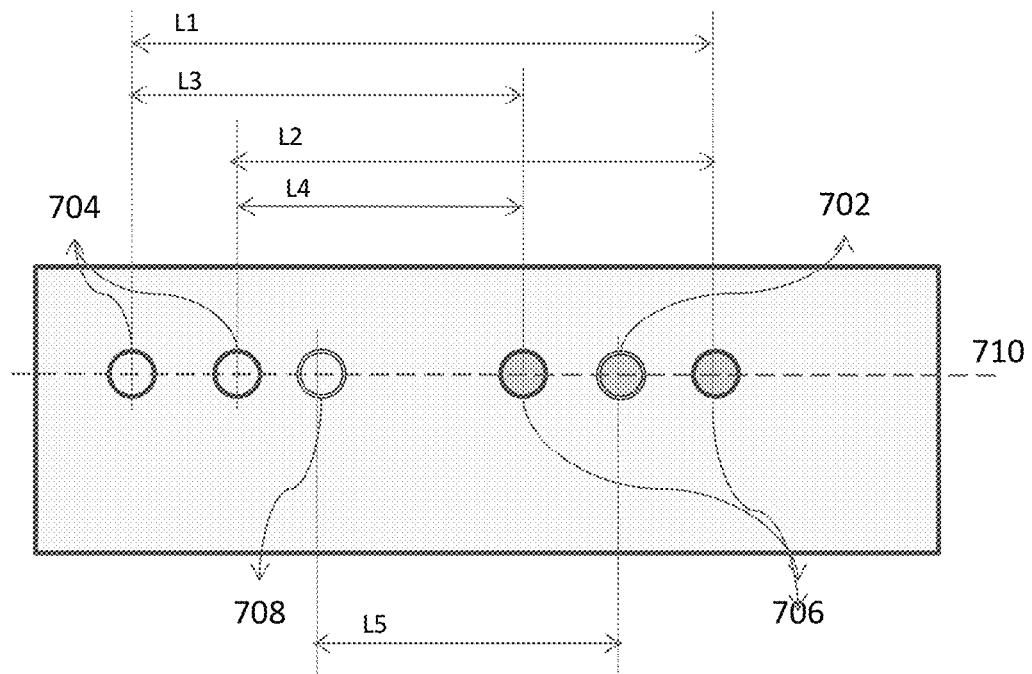
FIG. 7 is another exemplary schematic diagram of a probe of the present invention combining NIRS and DCS where the NIRS and DCS fibers are all within a single line.

FIG. 7 shows another embodiment for the combination of NIRS and DCS that is particularly useful for simultaneous measurements. In this embodiment, the linear arrangement between each of the four probes is shown. Thus, the DCS source (702) is in line with the DCS detector (708), the NIRS sources (706) are in line with the NIRS detector (704) and both the NIRS and DCS sources and detectors are found on a single linear line (710).

Figure 8:
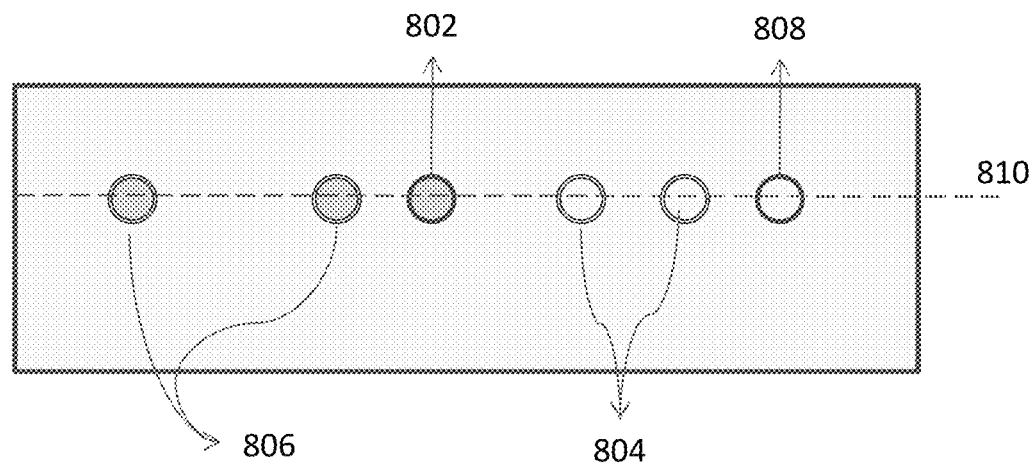
FIG. 8 is another exemplary schematic diagram of a probe of the present invention combining NIRS and DCS where the NIRS and DCS fibers are all within a single line In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

FIG. 8 shows yet another embodiment for the combination of NIRS and DCS having a linear arrangement between each of the probes. Thus, the DCS source (802) is in line with the DCS detector (808), the NIRS sources (806) are in line with the NIRS detector (804) and both the NIRS and DCS sources and detectors are found on a single linear line (810). The probe exemplified in FIG. 8 has dimensions of 4×1.5×2 cm.

In some embodiments, the various optical fibers are aligned linearly, and arranged such that they substantially form a line. In some embodiments, the location of the different optical fibers onto the probe tip is determined as follows: first, select the optical fiber having the widest diameter. Then, draw a line between the centers of the optical fiber having the widest diameter ($d_{wide}$) and the optical fiber which make a pair with the optical fiber having the widest diameter. For example, if the diameter of the NIRS detector fiber is the widest, the line between the centers of the NIRS detector and source fibers is drawn. The distal ends of each of the other fibers are placed on the probe tip in a linear arrangement and are at a location such that they are placed on or near this line. In some embodiments, the probe body contains fiber bundles that are bent at 90 degree angles. In other embodiments, the fiber bundles are bent at more or less than 90 degrees, such as at greater than 45 degrees.

Thus, in some embodiments, each of the optical fibers is arranged so that the fibers are aligned linearly (they substantially form a line). Each of the optical fibers may be centered or substantially centered on the line described above. Alternatively, the different optical fibers may be offset from the center line but still lay on a line that is defined as having a line width as wide as the widest diameter fiber optic. For example, the maximum offset from the center of the line for a fiber having a diameter $D_2$ is $\frac{1}{2}(d_{wide}-d_2)$. In other embodiments, the optical fibers may be offset from the center line of the line described above such that at least half of the fiber area is within the line width. For example, the maximum offset from the center of the line for a fiber having a diameter $d_2$ is $\frac{1}{2}d_{wide}$.

In practice, a probe tip that is configured such that the DCS and NIRS sources and the DCS and NIRS detectors are at the same location is an optimal configuration from the perspective of sampling the tissue. While realizing this design can be challenging from the instrument configuration perspective, the present disclosure provides an optimal means for making a probe tip having this configuration using the filtering strategy wherein the DCS wavelength (e.g., the third wavelength) is either longer or shorter than the NIRS wavelengths (e.g., at least the first and second wavelengths). In some embodiments, one or more, or even all of the optical waveguides are bent near the probe tip. This can provide easier fabrication.

Preferably, the probe tip has a substantially flat surface that interfaces with the tissue sample. This allows for more accurate sampling. To aid in fabrication and use of the device, the probe may be designed such that the waveguides, which may be optical fibers, exit from the side of the probe at approximately 90 degrees to maintain a low probe profile when placed against the head or other tissue.

Various numbers of sources and detectors and thus source-detector distances may be used within the scope of the present invention. In some embodiments, there are two or more source-detector distances for the NIRS light at the probe tip. Thus, the first and second waveguides are located at discreet distances from the fourth optical waveguide. Alternatively, the first waveguide is located discreet distance from both the fourth optical waveguide and an additional waveguide configured to transmit SO2 lights scattered from tissue. Each of the first and second waveguides (and optionally further waveguides), may transmit a single or multiple wavelengths of light.

In some embodiments, there are four or more source-detector distances for the NIRS light at the probe tip. Thus, the first and second waveguides are located at discreet distances from the fourth optical waveguide and from at least one additional waveguide that is configured to transmit SO2 lights scattered from the tissue. Each of the first and second waveguides (and optionally further waveguides), may transmit a single or multiple wavelengths of light.

In some embodiments, there are two or more source-detector distances for the DCS light at the probe tip. Having two or more source-detector distances has benefits, particularly in pediatric and adult patients when both a short and a long separation are needed. Thus, in some embodiments, there is a fifth optical waveguide and an additional optical waveguide configured to transmit the CBF light scattered from the tissue that are at different discreet distances from the third optical waveguide at the probe tip. In yet other embodiments, there is an additional optical waveguide configured to deliver a CBF light towards the tissue, wherein this additional optical waveguide is located at a different source-detector distance than the distance between the third and fifth waveguides at the probe tip.

Accordingly, the present invention provides an advantage over the known art in that NIRS and DCS measurements can be operated at the same location simultaneously and there is no need to move the probe between NIRS and DCS measurements.

Additionally, during calibration of the probe, both the NIRS and DCS portions may be calibrated without moving the probe, and may be calibrated simultaneously.

These source-detector separations may be chosen to optimize the various depths of penetration for the DCS measurement. In some examples, source-detector separations of, for example 1.5 cm, 2 cm, 2.5 cm, 3.0 cm, 3.5 cm, and 4.0 cm are chosen. In some embodiments, a source-detector separation of 3.0 cm or less is preferred.

In some embodiments, the integrated device includes an optical scatterer between the distal end of the third optical fiber and probe tip. This is particularly useful to attenuate the CBF light to a level that is safe for continued exposure on skin. An exemplary optical scatterer is piece of Teflon® such as a thin Teflon® disk.

Wavelengths

Previously, eight different wavelengths within the wavelength range from 660 to 830 nm were used for SO2 detection along with a single wavelength for the CBF light is 785 nm. Eight SO2 lights are detected via a fiber optics light guide by a photomultiplier tube (PMT). This reference describes the additional measurement of DCS data where the DCS is performed after the NIRS data is obtained. The CBF light is detected via a single mode fiber (SMF) by a photon-counting avalanche photodiodes (APD). The detection efficiency of DCS is smaller than that of NIRS, because the coupling efficiency of SMF is smaller than that of the fiber optics light guide. Therefore, the incident power of CBF light to the tissue is higher than that of the SO2 light. For example, the incident power of SO2 light to the tissue is about 3 mW and that of CBF light is about 20 mW. In some embodiments the SO2 light is modulated at, for example, a frequency of 110 MHZ.

$CMRO_2$ is estimated from $StO_2$ measured by NIRS and $CBF_i$ measured by DCS. In order to calculate $CMRO_2$ having high temporal resolution, $StO_2$ and $CBF_i$ should be measured simultaneously. However, in Lin et al., the wavelength used for DCS measurements (CBF light) was set within the NIRS range (SO2 light). Therefore, it is impossible to measure both DCS and NIRS at the same time.

In order to acquire $CMRO_2$ having high temporal resolution, NIRS and DCS measurements should be operated simultaneously. In order to do that, the wavelength of CBF light is set out of the SO2 light wavelength range. For example, the wavelength of CBF light may be greater than or shorter than the wavelengths of each of the SO2 lights. In one embodiment, the CBF light is separated from the SO2 light and is at a longer wavelength than each of the NIRS wavelengths.

Thus, in one embodiment, the wavelengths of eight SO2 lights are 660, 670, 690, 705, 730, 780, 808, and 830 nm and the wavelength of CBF light is 850 nm. In another embodiment, the wavelength of the CBF light is 670 nm and the SO2 lights are at 690, 705, 730, 780, 808, and 830 nm. In each of these embodiments, fewer or more SO2 lights may be used. In some embodiments, the eight SO2 lights come from eight SO2 sources. Alternatively, fewer sources may be used.

In some embodiments, the CBF light has a wavelength that is greater than the wavelengths SO2 light. This is particularly advantageous since, as DCS generally uses a single mode fiber, much less light can be coupled into the detection fiber. Thus, it is advantageous to select a wavelength with greater scattering efficiency for the CBF light, or longer wavelength light.

In some embodiments, the CBF light is spectrally separated from the SO2 light. For example, the CBF light is at least 10 nm, or at least 15 nm, or at least 20 nm longer than any SO2 wavelength. In other examples the CBF light is at least 10 nm, or at least 15 nm, or at least 20 nm shorter than any SO2 wavelength.

Figure 2:
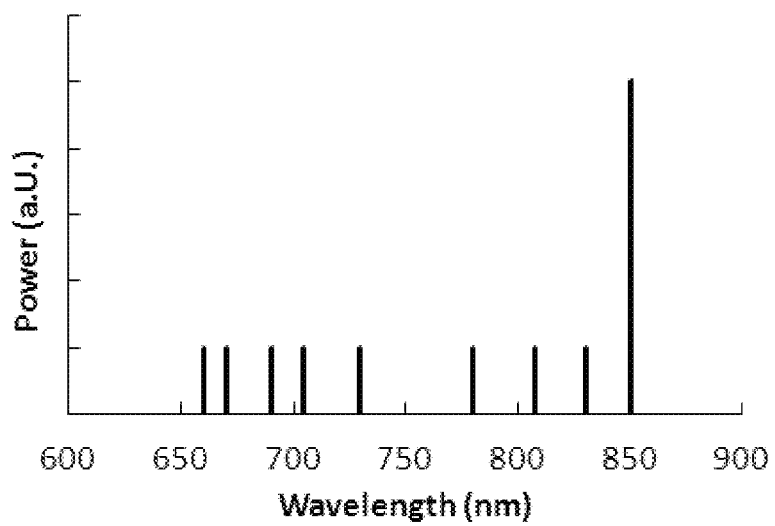
FIG. 2 illustrates an exemplary wavelength arrangement of NIRS and DCS signals.

An optical filter may be placed in front of the detector for NIRS measurement to attenuate the CBF light in order to prevent the CBF light from substantially affecting the NIRS measurement. For example, where the wavelengths of eight SO2 lights are 660, 670, 690, 705, 730, 780, 808, and 830 nm and the wavelength of CBF light is 850 nm (FIG. 2), a low pass filter blocking light at 850 nm and above may be used. Alternatively, a notch filter may be used.

Similarly, an optical filter may be placed in front of the detector for DCS measurement to attenuate SO2 light at one or more of the NIRS wavelengths in order to prevent the SO2 light from substantially affecting the DCS measurement.

In some embodiments, in addition to or in replace of optical filter(s), the signal is filtered using signal processing.

In some embodiments, the device does not contain a filter located between the probe tip and the DCS detector. This embodiment is particularly useful in instances where the light intensity of the CBF light is large compared to the light intensity of each of the SO2 lights. For example, in one embodiment, the CBF light is at least 10-fold more powerful than any of the SO2 light and a filter blocking the CBF light is found in front of the detector set to analyze SO2 light and no filter is found in front of the detector set to analyze CBF light.

As used herein, the term "substantially," when used in context of substantially attenuating light, means that the intensity of the light is decreased by at least 70%, or more preferably at least 80%, or more preferably at least 85%, or more preferably at least 50%, or more preferably at least 95%, or more preferably at least 97%, or more preferably at least 99%.

In some embodiments, the integrated device comprises a first and a second waveguide, each delivering at least one SO2 light to the tissue. The device may comprise a fiber bundle where the two different wavelengths are delivered via two different fibers in a fiber bundle. Multiple additional wavelengths of SO2 light may also be delivered via fibers in the fiber bundle. In some embodiments, both the first and second waveguides deliver at least two wavelengths, where the two waveguides may both transmit the same wavelengths. For example, the first waveguide transmits four wavelengths within the range of 660 and 910 nm and the second waveguide transmits four wavelengths within the range of 660 and 910 nm, where there are eight unique NIRS wavelengths. In another example, the first waveguide transmits four wavelengths within the range of 660 and 910 nm and the second waveguide transmits the same four wavelengths. In other examples, each waveguide delivers 3, 5, 6, 7, or 8 different wavelengths.

In some other embodiments, the integrated device comprises a first waveguide configured to deliver at least two SO2 lights to the tissue. The two different wavelengths of light can be combined into a single waveguide via an optical splitter or coupler, an optical combiner, an optical switch, or by any other means known in the art to combine two or more different wavelengths into a single optical waveguide.

FIG. 3 shows the schematic diagram of NIRS and DCS measurement system. Eight SO2 lights are emitted from the laser diodes and incident to the tissues via an optical fiber bundle. The laser system with the long coherent length is used for a DCS laser source. The CBF light is incident to the tissue via an optical fiber. Those lights are scattered in the tissue. A part of the scattered SO2 light is collected by an optical fiber light guide. The optical shortpass filter is inserted between the optical fiber light guide and a PMT in order to attenuate the CBF light. The cutoff wavelength of the shortpass filter is set between the wavelengths of the SO2 light at the longest wavelength and the CBF light. A part of the scattered CBF light is collected by a single mode fiber. The optical longpass filter may be inserted between the single mode fiber and the APD in order to attenuate the SO2 lights. The cutoff wavelength of the longpass filter is set between the wavelengths of the SO2 light at the longest wavelength and the CBF light. If the incident power of CBF light is higher than that of SO2 light sufficiently, the optical longpass filter in front of APD for DCS measurement may not be needed.

To perform NIRS, several wavelengths are used. On the other hand, one wavelength is necessary in the DCS measurement. In order to acquire NIRS and DCS signals simultaneously, the wavelength used for the two modalities should be different. The wavelength of CBF light is arranged out of the NIRS wavelength range. In one embodiment, the wavelength of the CBF light is longer than the wavelengths of SO2 lights.

In some embodiments, a filter used for eliminating unwanted light from the DCS excitation source is put in front of the detector for NIRS in order to prevent light from the DCS excitation or scatter to hit the detector(s) for the SO2 light. This filter may be, for example an optical shortpass filter. Preferably, the cutoff wavelength of the optical shortpass filter is set between the longest wavelength of SO2 light and the wavelength of CBF light.

HGB Concentration

Hemoglobin concentration can be measured by any means known in the art, such as by a standard blood test. [HGB] is among the most commonly performed blood tests and is usually part of a complete blood count.

Arterial Oxygenation $SaO_2$ is the arterial oxygenation, or arterial oxygen saturation. $SaO_2$ provides percentage of hemoglobin binding sites in the bloodstream that are occupied by oxygen. This variable can be measured by any means known in the art. In one embodiment, a pulsed oxymeter is used. A pulse oxymeter measures the light absorption characteristics of saturated hemoglobin to measure oxygen saturation. The pulsed oxymeter may be integrated into the device as described herein or it may be a separate device commonly used by doctors and technicians.

DEFINITIONS

As used herein, the term "simultaneous," when used in connection with simultaneously measuring means that the measurements are taken within the span of a single heartbeat and thus within the span of substantive change in oxygenation. In some embodiments, simultaneous means less than 5 sec., less than 4 sec., less than 3 sec., less than 2 sec., less than 1 sec., less than 500 msec., or less than 200 msec. In yet other embodiments, simultaneous measurements mean that both the SO2 light and the CBF light are incident on the tissue of a subject at the same time where the CBF light does not have to be blocked or turned off in order to perform a measurement using the SO2 light and vice versa.

In some embodiments, simultaneous detection means that the first detector detects light at the first and/or second wavelengths at the same time that the second detector detects light at the third wavelength. This can be done without switching the CBF light off. Thus, the term simultaneous includes embodiments where both the CBF light source and the SO2 light source are turned on at the same time.

It should be understood that the light transmitted from a substrate such as a tissue that is described herein is only a quantity of the total scattered and/or reflected light. Much of the total scattered and/or reflected light will not be captured by the apparatus as described herein and is not measured.

As used herein "temporal resolution" refers to the precision of a measurement with respect to time. Oxygen saturation and blood flow vary over time. In order to estimate more exact oxygen consumption, oxygen saturation should be measured at the same time with the blood flow. Employing this invention, the temporal resolution can be decrease compared with that shown by Lin et al.

As used herein, the phrase "greater than the peak intensities" means that the value is greater than the average of the peak intensities, not any instantaneous peak intensity. It is understood that fluctuations may occur in the signal intensity and that such fluctuations may be smoothed to provide a more stable value for peak intensity.

In referring to the description, specific details are set forth in order to provide a thorough understanding of the examples disclosed. In other instances, well-known methods, procedures, components and circuits have not been described in detail as not to unnecessarily lengthen the present disclosure.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The term "about," as used herein means between 0 and 10% of the value or more preferably between 0 and 5% of the value.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

Exemplary embodiments are described with reference to the several drawings, wherein like reference numerals designate identical or corresponding parts throughout the several views and embodiments. Accordingly, descriptions of such parts with like reference numerals are not be repeated with respect to multiple figures.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

EXAMPLES

Example 1

Hybrid FDNIRS-DCS Instrument

A hybrid FDNIRS-DCS instrument was built having dimensions of approximately 23" (l)×18" (w)×9" (h). The FDNIRS portion of the instrument has 16 radio frequency (110 MHz) modulated laser diodes operating at 8 different wavelengths ranging from 670-830 nm and two photomultiplier tube detectors (PMT) for heterodyne detection (similar to the Imagent from ISS, Inc). The DCS component of the instrument has a long-coherence length 852 nm laser, 4 low dark-count photon counting avalanche photodiodes, and a custom-made 256-tau correlator board. A notch filter was placed in front of the FDNIRS PMTs.

Furthermore, to customize this instrument for use in full-term neonates, the rigid linear optical probe tip of FIG. 8 was used. The probe body in this embodiment contained four FDNIRS fiber bundles bent at 90 degree angles and providing four source-detector separations for FDNIRS (1.5, 2.0, 2.5, and 3.0 cm). For DCS, 2 right angle prisms separated by 2.0 cm may be used to deliver and collect light to/from the tissue surface. At the DCS detection prism, four single mode fibers are bundled together and their signals are averaged to improve the signal-to-noise ratio.

This system, along with in-house designed software enables simultaneous FDNIRS/DCS measurements. In use, the FDNIRS component has a dynamic range of 35 dB (10 log 10, presuming the FDNIRS voltage is proportional to the optical power). At a PMT gain of 550 V, i.e. a typical gain for operation in the clinic, the minimum detection limit is 0.032 pW/√Hz with 0.35°/√Hz phase noise at a signal level of 10 pW. Over 60 minutes, the AC amplitude is stable to within 0.7% and the phase is stable to within 0.2°.

During simultaneous FDNIRS and DCS operation, there was minimal crosstalk between the two modalities thanks to the use of the notch filter in front of the PMTs. Although the DCS intensity and beta (a coherence factor) are affected by the FDNIRS lasers, the FDNIRS lasers have a negligible effect on the measured blood flow index.

EXEMPLARY REFERENCES

David A. Boas, *Handbook of Biomedical Optics*, CRC Press, 2011.

Durduran, T., et al., Diffuse optics for tissue monitoring and tomography. *Reports on Progress in Physics*, 2010. 73(7): 43.

Franceschini M. A., et al., Assessment of infant brain development with frequency-domain near-infrared spectroscopy. *Pediatric Research* 2007. 61: 546-551.

Grant, P. E., et al., Increased cerebral blood volume and oxygen consumption in neonatal brain injury. *Journal of Cerebral Blood Flow and Metabolism* 2009. 29: 1704-1713.

Lin, P. Y., Roche-Labarbe, N., Dehaes, M., Carp, S., Fenoglio, A., Barbieri, B., et al. Non-invasive Optical Measurement of Cerebral Metabolism and Hemodynamics in Infants. *J. Vis. Exp.* (73), e4379, doi:10.3791/4379, 2013.

Peyman Zirak et al., Effects of acetazolamide on the micro- and macro-vascular cerebral hemodynamics: a diffuse optical and transcranial Doppler ultrasound study, *Biomedical Optics Express*, Vol. 1, No. 5, pp. 1443-1456, 2010.

Roche-Labarbe, N., et al., Near-infrared spectroscopy assessment of cerebral oxygen metabolism in the developing premature brain. *Journal of Cerebral Blood Flow and Metabolism* 2012. 32: 481-488.

Gagnon et al., Neuriomage 2012; 59(4) 3933-3940.

Strangeman, Li, and Zhang, (201) PLOS One, 8(8) e66319.

Nadege Roche-Labarbe et al., Journal of Cerebral Blood Flow & Metabolism (2012) 32, 481-488.

While the present invention has been described with reference to exemplary embodiments, it is to be understood that the invention is not limited to the disclosed exemplary embodiments. The scope of the invention is to be accorded the broadest interpretation so as to encompass all such modifications and equivalent structures and functions.

Thus, we claim herein a device comprising any feature described, either individually or in combination with any feature, in any configuration and further claim a method of use comprising any process described, in any order, using any modality as described herein.

The following claims further describe aspects of the invention.

The invention claimed is:

1. An integrated device comprising:
a first optical waveguide configured to deliver light at a first wavelength towards a tissue;

and wherein the first optical waveguide is configured to deliver light at a second wavelength towards the tissue or wherein the device contains a second optical waveguide configured to deliver light at the second wavelength towards the tissue, wherein each of the lights of the first and second wavelengths and any additional wavelengths configured for absorption spectroscopy are referred to as SO2 light;

a third optical waveguide configured to deliver a light at a third wavelength that is different than the wavelengths of the SO2 lights towards the tissue, the light at a third wavelength is referred to as CBF light, and where the third wavelength is either longer or shorter than each of the wavelengths of the SO2 lights;

a fourth optical waveguide configured to transmit one or more of the SO2 lights scattered from the tissue;

a fifth optical waveguide configured to transmit the CBF light scattered from the tissue; and a narrow probe tip coupled to the distal end of each of the first, second (if present), third, fourth, and fifth optical waveguides (all the waveguides), wherein the distal ends of all these waveguides are aligned to form a line at the narrow probe tip;

wherein the integrated device detects the SO2 and CBF lights simultaneously.

2. The integrated device of claim 1, wherein the first and second wavelengths are within the range of 660 to 910 nm.

3. The integrated device of claim 1, further comprising:
a first detector, in optical communication with the fourth optical waveguide, configured to detect the SO2 lights; and
a second detector, in optical communication with the fifth optical waveguide, configured to detect the CBF light scattered from the tissue.

4. The integrated device of claim 3, further comprising a processor adapted to quantify temporal intensity fluctuations in detected light by the second detector.

5. The integrated device of claim 4, wherein the processor is capable of determining oxygen consumption using data obtained from analyzing the SO2 lights and the CBF light.

6. The integrated device of claim 5, wherein the oxygen consumption is determined using the following parameters:
hemoglobin concentration, as determined by a blood test,
blood flow index, as determined by measuring the CBF light,
arterial oxygenation, as determined using a pulse oximeter, and
tissue oxygenation, as determined by measuring the SO2 lights.

7. The integrated device of claim 6, wherein the oxygen consumption ($CMRO_2$) is determined using the equation:

$$CMRO_2 = \frac{HGB \times CBF_i \times (SaO_2 - StO_2)}{4 \times MW_{Hb} \times \beta}$$

wherein:
HGB is hemoglobin concentration,
$CBF_i$ is cerebral blood flow index,
$SaO_2$ is arterial oxygen saturation, and
$StO_2$ is tissue oxygen saturation,
$MW_{Hb}$ is the molecular weight of hemoglobin, and
$\beta$ is the percent concentration of the venous compartment to the hemoglobin oxygenation measurement.

8. The integrated device of claim 5, wherein the relative oxygen consumption ($rCMRO_2$) is determined using the equation:

$$rCMRO_2 = \frac{CMRO_2}{CMRO_{2o}} = \frac{HGB}{HGB_o} \cdot \frac{CBF_i}{CBF_{io}} \cdot \frac{SaO_2 - StO_2}{SaO_{2o} - StO_{2o}}$$

wherein:
HGB is hemoglobin concentration,
$CBF_i$ is cerebral blood flow index,
$SaO_2$ is arterial oxygen saturation,
$StO_2$ is tissue oxygen saturation, and
the subscript "o" is a reference.

9. The integrated device of claim 1, wherein the first optical waveguide and the second optical waveguide are both configured to deliver at least two different wavelengths of light towards the tissue.

10. The integrated device of claim 1, wherein the second optical waveguide is configured to deliver lights at the same wavelengths delivered by the first optical waveguide.

11. The integrated device of claim 10, further comprising a sixth optical waveguide configured to transmit one or more SO2 lights scattered from the tissue.

12. The integrated device of claim 1, wherein the first waveguide delivers light at at least eight wavelengths.

13. The integrated device of claim 1, wherein the separation between the distal end of the first optical waveguide and the distal end of the fourth optical waveguide and the separation between the distal end of the third optical waveguide and the distal end of the fifth optical waveguide are chosen to optimize the depth of penetration of scattered light having a wavelength between 660 and 910 nm.

14. The integrated device of claim 1, wherein the separation between the distal end of the first optical waveguide and the distal end of the fourth optical waveguide is up to 4.0 cm and wherein the separation between the distal end of the third optical waveguide and the distal end of the fifth optical waveguide is up to 4.0 cm.

15. An integrated device comprising:
a first optical waveguide configured to deliver light at a first wavelength towards a tissue;
and wherein the first optical waveguide is configured to deliver light at a second wavelength towards the tissue or wherein the device contains a second optical waveguide configured to deliver light at the second wavelength towards the tissue, wherein each of the lights of the first and second wavelengths and any additional wavelengths configured for absorption spectroscopy are referred to as SO2 light;

a third optical waveguide configured to deliver a light at a third wavelength that is different than the wavelengths of the SO2 lights towards the tissue, the light at a third wavelength is referred to as CBF light, and where the third wavelength is either longer or shorter than each of the wavelengths of the SO2 lights;

a fourth optical waveguide configured to transmit one or more of the SO2 lights scattered from the tissue;

a fifth optical waveguide configured to transmit the CBF light scattered from the tissue; and a probe tip coupled to the distal end of each of the first, second (if present), third, fourth, and fifth optical waveguides (all the waveguides), wherein the distal ends of all these waveguides are aligned linearly at the probe tip;

wherein the integrated device detects the SO2 and CBF lights simultaneously, and wherein a center line on the probe tip is defined as between the center of the optical waveguide having the widest diameter ($d_{wide}$) and the optical waveguide that makes a source-detector pair with the optical waveguide having diameter $d_{wide}$ and wherein the offset from the center line to the center of each of the first, second, third, fourth, and fifth optical waveguides is equal to or less than ½ $d_{wide}$.

16. The integrated device of claim 15, wherein the center of each of all the optical waveguides is equal to or less than ½ ($d_{wide}$ –the waveguide diameter) away from the center line.

17. An integrated device comprising:
a first light source that comprises one or more light sources transmitting SO2 light having at least a first wavelength within the range of 660 to 910 nm and a second wavelength within the range of 660 to 910 nm;
one or more waveguides configured to direct the SO2 light towards a tissue;
one or more detectors (first detector) configured to detect the SO2 light which is scattered from the tissue;
a second light source having a third wavelength that is greater than each of the wavelengths of SO2 light (CBF light);
a waveguide configured to direct the CBF light towards a tissue;
a second detector configured to detect light scattered from the tissue at the third wavelength;
wherein the distal ends of all the waveguides are aligned to form a narrow line;
a processor adapted to quantify temporal intensity fluctuations in detected CBF light; wherein the integrated device detects the SO2 light and CBF light simultaneously.

18. The integrated device of claim 17, wherein the second light source has an average light intensity that is greater than the average light intensities of the first light source.

19. The integrated device of claim 17, wherein the first light source comprises a plurality of laser diodes and the second light source comprises a laser.

20. The integrated device of claim 17, further comprising a probe adapted to measure cerebral tissue oxygenation (StO$_2$ probe) and a probe adapted to measure cerebral blood flow index (CBF$_i$ probe), wherein the StO$_2$ probe comprises the one or more waveguides configured to direct the SO2 light towards a tissue and the first detector; and the CBFi probe comprises the waveguide configured to direct the CBF light towards a tissue and the second detector.

21. A method of simultaneously measuring cerebral tissue oxygenation (StO$_2$) and cerebral blood flow index (CBF$_i$) in a tissue of a subject comprising:
providing a device comprising:
a first light source to transmit at least two lights (SO2 lights), having at least two different wavelengths within the range of 660 to 910 nm;
one or more waveguides configured to direct the SO2 lights towards the tissue:
a second light source to transmit a third light, wherein the third light has a third wavelength that is greater than each of the wavelengths of the SO2 lights;
a waveguide configured to direct the third light towards the tissue;
wherein the distal ends of all the waveguides are aligned to form a narrow line;
at least one detector to detect the SO2 lights and the third light after they have traveled through the tissue and to sense a quantity of the light intensity scattered from the tissue at the third wavelength; and
a processor; and
simultaneously determining StO$_2$ and CBF$_i$, wherein:
determining StO$_2$ in the tissue of the subject comprises the steps:
transmitting SO2 lights into the tissue,
detecting the lights after they have traveled through the tissue, and
using the processor to determine the difference between the intensity of the transmitted light and the detected light at each of the at least two different wavelengths, and
determining the difference in attenuation to obtain StO$_2$; and
determining CBF$_i$ in the tissue of the subject comprises the steps:
simultaneously transmitting the third light into the tissue, sensing a quantity of the light intensity scattered from the tissue at the third wavelength,
using the processor to determine the CBFi based on the quantity of the CBF light intensity which is scattered from the tissue.

* * * * *